United States Patent [19]

Biber

[11] Patent Number: 5,126,877

[45] Date of Patent: Jun. 30, 1992

[54] ILLUMINATION SYSTEM FOR A SURGICAL MICROSCOPE

[75] Inventor: Klaus Biber, Aalen, Fed. Rep. of Germany

[73] Assignee: Carl-Zeiss-Stiftung, Heidenheim, Fed. Rep. of Germany

[21] Appl. No.: 754,591

[22] Filed: Sep. 4, 1991

[30] Foreign Application Priority Data

Sep. 8, 1990 [DE] Fed. Rep. of Germany ....... 4028605

[51] Int. Cl.⁵ .............................................. G02B 21/00
[52] U.S. Cl. .................................. 359/389; 359/385
[58] Field of Search ........................ 359/385, 388, 389

[56] References Cited

U.S. PATENT DOCUMENTS 4,779,968 10/1988 Sander ................................. 359/389

Primary Examiner—Robert J. Pascal
Attorney, Agent, or Firm—Eugene Stephens & Associates

[57] ABSTRACT

Disclosed is an illumination system for a surgical microscope comprising an illumination assembly (1), which is located outside the optical axis (2a) of the microscope lens, and two reflecting mirrors (4,6) which are located behind the illumination assembly, each directing respective portions of the illumination light to the operating area. The first reflecting mirror (4) directs its portion of the light onto the operating area at an oblique angle (preferably 6°) relative to the viewing axis (2) of the microscope lens. The position of the second reflecting mirror (6) can be adjusted so that its portion of the light is directed to the operating area along a different path that is either (a) coincident with said viewing axis or (b) oblique to the axis at an angle closer than that formed by the path of the light directed by the first reflecting mirror (i.e., between 0° and 6°). By means of respective diaphragm mechanisms (11,12) associated with each of the reflecting mirrors, the two portions of the light may be individually adjusted to control contrast and/or to select (i) 0° illumination, (ii) oblique illumination, or (iii) various combinations of both types of illumination.

8 Claims, 2 Drawing Sheets

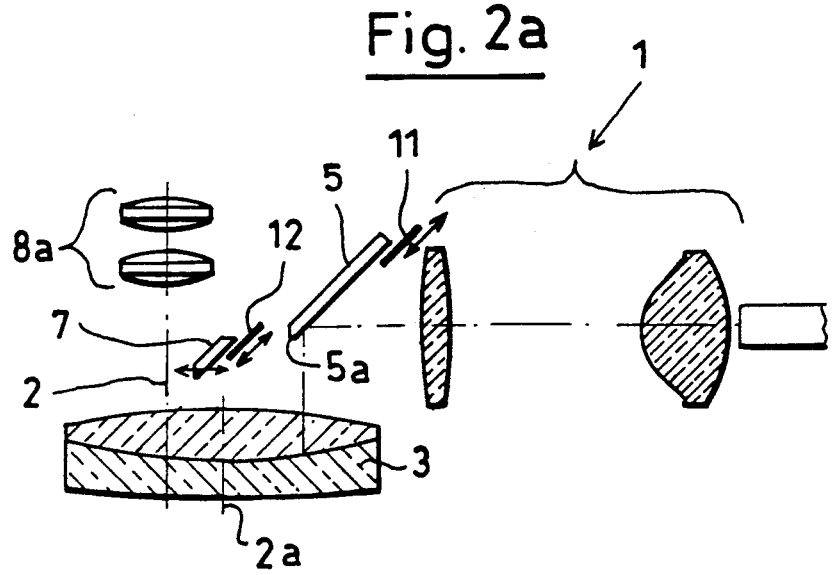
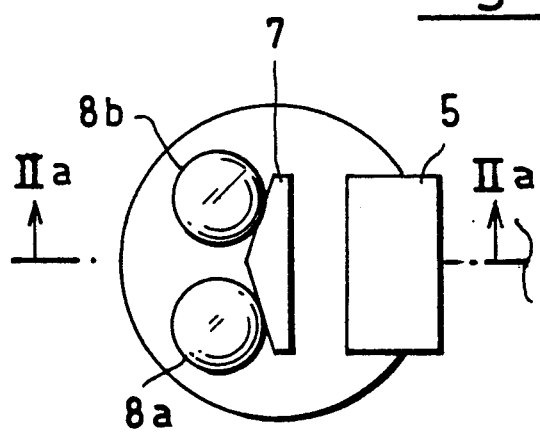

ILLUMINATION SYSTEM FOR A SURGICAL MICROSCOPE

TECHNICAL FIELD

The invention relates to illumination systems for surgical microscopes in which the illuminating light is directed through the microscope lens to the object point.

BACKGROUND

Depending on the medical field, microscopes used during surgery must meet different requirements insofar as the illumination of the operating area is concerned. The type of illumination is determined substantially by the angle formed by the axis of the illumination beam and the axis of the microscope lens.

In microsurgery in non-ophthalmic fields, e.g., otolaryngological surgery and neurosurgery, the operating area is illuminated obliquely with light directed along a path close to the lens axis. This is referred to in the art as "coaxial illumination", and it reduces the diameter of the illuminated area to so-called spot illumination, which can be directed into narrow, deep body cavities.

However, for microsurgical procedures on the eye, some microscopes have projected the illumination vertically, i.e., along the optical axis of the microscope lens, onto the operating area. With this latter type of illumination, known as "0° illumination", the vertically impinging light rays are diffusely reflected by the retina, and this reflected illumination makes the capsule of the lens (i.e., the shell of the lens of the eye) appear in reddish transmitted light. As a result of this, tissue remainders which must be removed by suction from the eye lens are rendered visible by high contrast.

Nonetheless, such vertically impinging light is required only during a portion of the ophthalmic surgical procedure or as partial illumination, so there is often a need to illuminate the patient's eye with either or both vertical and oblique impinging light during ophthalmic surgery.

The present invention meets this need with a special system for surgical microscopes which can provide either or both vertical and oblique illumination in combinations selected by the operator.

SUMMARY OF THE INVENTION

In accordance with the present invention, a first reflecting element is located in front of the optical axis of the microscope lens and is configured to reflect only a portion of the illuminating light toward the object point in an oblique path close to the axis. A second reflecting element, located on or behind the optical axis of the microscope lens, reflects another portion of the illuminating light toward the object point along either (a) a vertical path coincident with the lens axis or (b) an oblique path which is closer to the axis than the path of the light directed by the first reflecting element.

In the preferred embodiments of the present invention, the first reflecting element directs the illumination at an angle of inclination $\alpha$ of 6° relative to the optical axis of the viewing system and the second reflecting element reflects the illumination light toward the object point at an angle $\alpha$ that can be varied between 0° and 6° relative to the optical axis.

A first preferred embodiment of the invention herein is illustrated in FIGS. 1 and 1a and is characterized in that the first reflecting element is configured as a plane mirror with a cutout allowing part of the illuminating light to pass to the second reflecting element. The latter is configured as a plane mirror that fits in the space between the microscope's two binocular viewing systems.

In a second preferred embodiment of the invention herein, shown in FIGS. 2 and 2a, the first reflecting element is a plane mirror arranged so that part of the illuminating light passes below its lower edge to impinge on the second reflecting element, the latter being configured as a plane mirror positioned spatially in the optical path in front of the binocular viewing system.

In the preferred embodiments, the second reflecting element is arranged for adjustment perpendicular to the optical axis; and variable diaphragms are interposed between the illumination system and the reflecting elements so that variable portions of the light (a) may be directed to the object point via each of the reflecting mirrors or (b) may be masked out completely to provide illumination from only a selected one of the mirrors.

Two exemplary embodiments of the present invention are shown in the drawings and are described hereinafter.

DRAWINGS

FIG. 2 is a schematic illustration of a second preferred embodiment of the invention herein located in front of the main lens of a surgical microscope.

FIG. 2a is a sectional view of the illumination system of FIG. 2 along line IIa—IIa.

DETAILED DESCRIPTION

Figure 1A:
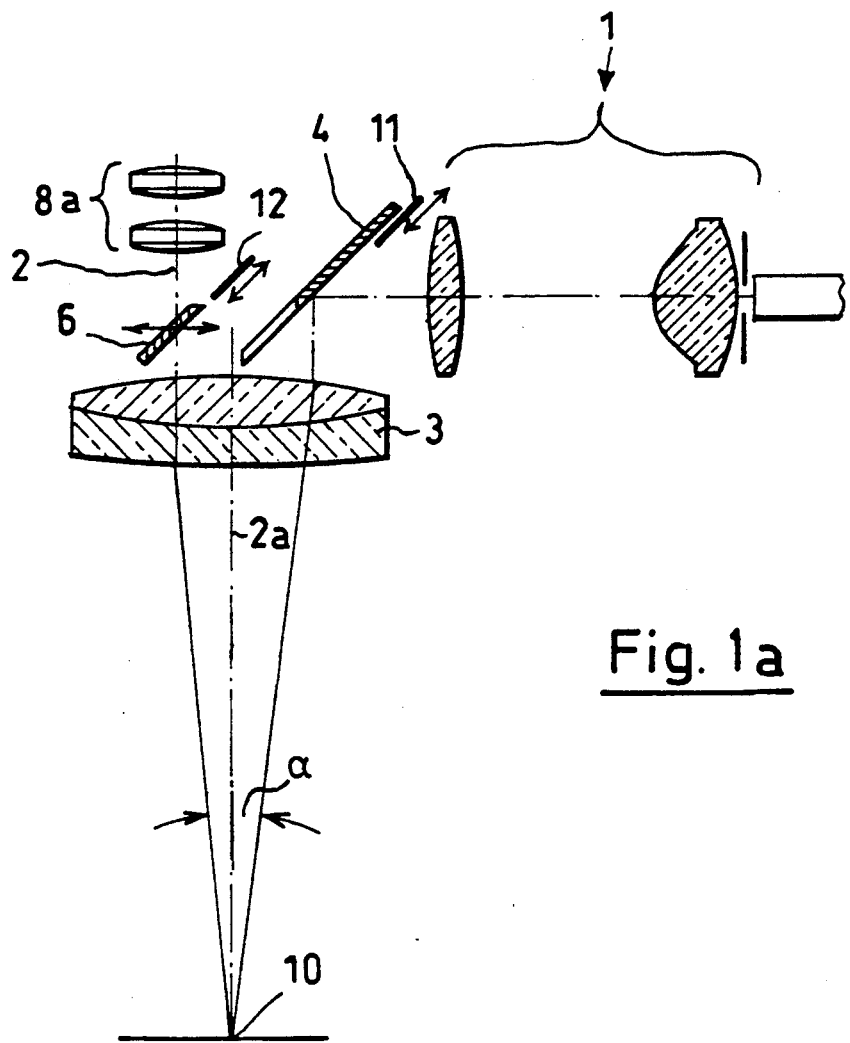
FIG. 1a is a sectional view of the illumination system of FIG. 1 taken along line Ia—Ia.
Figure 1:
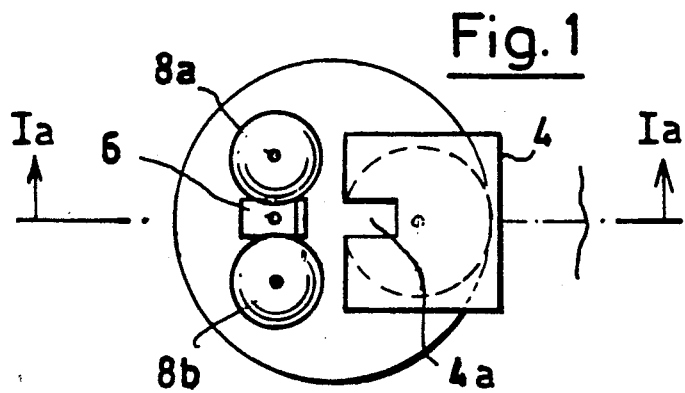
FIG. 1 is a schematic illustration of a first preferred embodiment of the invention herein located in front of the main lens of a surgical microscope.

The embodiments of the invention illustrated in FIGS. 1 and 2 each include a well-known microscope illumination assembly 1 comprising a light source and lenses as shown schematically. Interposed between illumination assembly 1 and the main lens 3 on the optical axis 2a of the surgical microscope is a reflection mirror 4,5 which directs the illuminating light onto the object point 10 along a path that is at an angle $\alpha$ relative to the optical axis 2 of the microscope's viewing system. Preferably the angle $\alpha$ is 6°. The reflecting mirror 4 has a cutout 4a through which a part of the illuminating light can pass to impinge on a reflecting mirror 6,7 which can be adjusted, preferably in a direction perpendicular to axis 2a. Depending on the adjusted position of reflecting mirror 6,7 (either on or outside axis 2a), that portion of the illuminating light impinging on reflecting mirror 6,7 is selectively directed to object point 10 along (a) a first path that is at an angle of 0° relative to viewing axis 2 or (b) along a second path at an angle to viewing axis 2 that is greater than 0° but less than the angle made by the oblique path followed by the light directed by first reflecting element 4,5.

By means of a diaphragm mechanism 11, the illumination cone of rays projected on object point 10 via reflecting mirror 4 can be masked progressively in order to increase the contrast. Also, a second diaphragm mechanism 12 is provided for mirror 6,7 and can be used to completely block out light impinging vertically on the patient's eye via reflecting element 6,7 if only oblique illumination close to the axis is desired.

In the illustrated preferred embodiments, the surgical microscopes have binocular viewing optics which are identified by reference numbers 8a and 8b; and in the embodiment shown in FIGS. 1 and 1a, mirror 6 is positioned between the binocular viewing systems.

A second preferred embodiment of the inventive illumination system is shown in FIGS. 2 and 2a, in which identical parts are identified by the same reference numbers as in FIGS. 1 and 1a. In this embodiment, reflecting elements 5 and 7 are constructed so that the lower edge of reflecting mirror 5 creates an upward limit for the illumination cone of rays impinging on reflecting mirror 7. It should be understood that the illumination cone of rays in the embodiment shown by FIG. 2a, even though not drawn completely, extends beneath main lens 3 to the observed object point 10 in a manner identical to that illustrated in FIG. 1.

The described illumination systems consequently permit the setting of three different types of illumination. Reflecting elements 6,7 and diaphragms 11,12 can be shifted in the direction of the arrows as indicated. When both reflecting mirrors 4,6 and 5,7 are respectively effective, a combination of both coaxial illumination and vertical 0° illumination can be adjusted. When the coaxial illumination is completely masked, only the 0° illumination is effective. When the 0° illumination is completely masked, only the coaxial illumination is effective. Intermediate stages of illumination are also possible by the progressive, continuously-variable masking of illumination rays. Main lens 3 may be centric or, as shown, eccentric relative to the axis of the viewing system.

I claim:

1. A system for illuminating the object point of the main lens in a surgical microscope comprising:
   an illumination assembly located outside the optical axis of said main lens;
   first reflecting element for reflecting light from said illumination assembly and directing the light through said main lens to the object point along a path close to said axis but oblique thereto, said first reflecting element being positioned between the illumination assembly and said optical axis and also being configured to reflect only a portion of said illuminating light; and
   a second reflecting element for reflecting a further portion of the light from said illumination assembly and directing said light through said main lens to the object point along one of (a) a first path coincident with said axis and (b) a second path oblique to said axis but closer thereto than the oblique path followed by the light directed by said first reflecting element.

2. The illumination system of claim 1 wherein the microscope has binocular viewing systems and said first reflecting element is a plane mirror with a cutout for allowing light to pass from said illumination assembly to said second reflecting element, and wherein said second reflecting element is also a plane mirror positioned between said binocular viewing systems.

3. The illumination system of claim 1 wherein the microscope has binocular viewing systems and said first reflecting element is a plane mirror having a lower edge and located to allow light from said illumination assembly to pass beneath said lower edge to said second reflecting element, and wherein said second reflecting element is a plane mirror positioned between said binocular viewing systems and said illumination assembly.

4. The illumination system of claim 1 wherein, when directing illuminating light along said first path, said second reflecting element is positioned on said axis, and wherein, when directing illuminating light along said second path, said second reflecting element is positioned outside said axis so that said axis is located between said first and second reflecting elements.

5. The illumination system of claim 1 wherein said second reflecting element is adjustable, perpendicular to said axis, to a plurality of positions between a first location in which the second reflecting element directs said light to the object point along said first path and a second location in which the second reflecting element directs said light along said second path.

6. The illumination system of claim 1 further comprising a pair of variable diaphragms interposed, respectively, between said illumination assembly and said first and second reflecting elements.

7. The illumination system of claim 1 wherein said oblique path followed by the light directed by said first reflecting element makes an angle of 6° with said axis, and wherein the first and second paths followed by the light directed by said second reflecting means make angles with said axis of (a) 0° and (b) less than 6°, respectively.

8. The illumination system of claim 1 wherein the microscope has an optical viewing axis eccentric relative to the axis of said main lens; wherein said oblique path followed by the light directed by said first reflecting element makes an angle of 6° with said optical viewing axis; and wherein the first and second paths followed by the light directed by said second reflecting means make angles with said optical viewing axis of (a) 0° and (b) greater than 0° but less than 6°, respectively.

* * * * *